(12) United States Patent
Patel et al.

(10) Patent No.: US 8,834,942 B2
(45) Date of Patent: Sep. 16, 2014

(54) ENHANCED ABSORPTION OF OREGANO DERIVED OILS

(75) Inventors: Bhiku Patel, Chandler, AZ (US); Robert L. Knechtel, Scottsdale, AZ (US)

(73) Assignee: PruGen IP Holdings, Inc., Scottsdale, AZ (US)

( * ) Notice: Subject to any disclaimer, the term of this patent is extended or adjusted under 35 U.S.C. 154(b) by 0 days.

(21) Appl. No.: 12/957,467

(22) Filed: Dec. 1, 2010

(65) Prior Publication Data

US 2012/0141616 A1 Jun. 7, 2012

(51) Int. Cl.
*A61K 36/00* (2006.01)
*A61K 36/55* (2006.01)
*A61K 36/53* (2006.01)

(52) U.S. Cl.
USPC .......................................... 424/745; 424/725

(58) Field of Classification Search
None
See application file for complete search history.

(56) References Cited

U.S. PATENT DOCUMENTS

| | | |
|---|---|---|
| 6,284,268 B1 | 9/2001 | Mishra et al. |
| 6,632,443 B2 | 10/2003 | Borowy-Borowski et al. |
| 7,273,624 B2 | 9/2007 | Rosenberg et al. |
| 2002/0077362 A1* | 6/2002 | Lee et al. .................. 514/560 |

FOREIGN PATENT DOCUMENTS

CN 101129334 A * 2/2008

OTHER PUBLICATIONS

Ke et al, Physical characterizations of microemulsion systems using tocopheryl polyethylene glycol 1000 succinate (TPGS) as a surfactant for the oral delivery of protein drugs, Journal of controlled release : official journal of the Controlled Release Society, (Feb. 2, 2005) vol. 102, No. 2, pp. 489-507.*
Eastman Chemical Company, Eastman Vitamin E TPGS NF—Applications and Properties, Oct. 2005, 22 pages, publication PCI-102B.
Arterburn, et al, Bioequivalence of Docosahexaenoic Acid from Different Algal Oils in Capsules and in DHA-Fortified Foods, Lipids, 2007, 1011-1024 (14 pages), vol. 42, Springer, USA.

* cited by examiner

*Primary Examiner* — Qiuwen Mi
(74) *Attorney, Agent, or Firm* — Dale F. Regelman; Quarles & Brady LLP

(57) ABSTRACT

A composition for increasing the bioavailability of oregano essential oil in humans and animals comprising mixing a first emulsifier and a second emulsifier in a ratio ranging from about 1:1 to about 3:1 with a consumable oil wherein the first emulsifier is polyoxyethylene sorbitan monooleate and the second emulsifier is tocopheryl polyethylene glycol succinate. Adding to that a second mixture of oregano essential oil and the first emulsifier in a ratio of 1:1.

13 Claims, 5 Drawing Sheets

US 8,834,942 B2

ENHANCED ABSORPTION OF OREGANO DERIVED OILS

I. INCORPORATION BY REFERENCE

This application incorporates by reference the full content of application Ser. No. 12/906,419 filed Oct. 18, 2010.

II. TECHNICAL FIELD

The present invention relates to the absorption and bioavailability of essential oregano oils consumed by humans or animals and, more particularly, to a composition that enhances the bioavailability of the oil through the mixing of the oil with certain emulsifiers.

III. BACKGROUND OF THE INVENTION AND PRIOR ART

Oregano is generally well known as a culinary spice. Less well known are the medicinal properties of oregano essential oil. Historically, Greek physicians used oregano essential oils for wounds, headaches, and venomous bites and even hemlock poisoning. It has also been used to treat lung conditions, bronchitis, sinusitis, and cold symptoms including cough. During the seventeenth century, it was heralded throughout Great Britain as an effective remedy for head colds. This was all based on anecdotal evidence.

Modern research has demonstrated that the medicinal properties of oregano essential oils may, in fact have scientific support inasmuch as research has shown oregano essential oils to have antiviral, antibacterial, antifungal, antiparasitic, and antiseptic properties. For non-limiting examples, in 1999, the Journal of Applied Microbiology compared 52 plant oils and extracts. Oregano essential oil was found to have significant antibacterial action against a wide number of bacteria including Staphlococcal species, *E. coli, Salmonella enterica*, and *Klebsiella pneumonie*. Staphlococcal infections are among the most common type of skin and soft tissue infections. The Methicillin-resistant *Staphylococcus aureus*, or MRSA, variety is one that is particularly difficult to eradicate even with the use of strong pharmaceutical antibiotics, and an infection can be fatal. Carvacrol (as described below, a major component of oregano essential oil), a phenolic compound found at a level approaching over 93% in Mediterranean oregano oil, may be effective against MRSA, the antibiotic-resistant "superbug" that is appearing in hospitals throughout the country. It does this without, apparently, creating mutant strains of drug-resistant bacteria, and it has none of the debilitating side effects of pharmaceutical antibiotics. See also, e.g., Journal Food Protection, Volume 64, July 2001 (Researchers at the Department of Food Science at the University of Tennessee reported that, among various plant oils, oil of oregano exhibited the greatest antibacterial action against common pathogenic germs such as Staph, *E. coli* and *Listeria*.); Journal Applied Microbiology, Volume 88, February 2000 (British researchers reported oregano oil had antibacterial activity against 25 different bacteria.); Southern Medical Journal, Volume 94, August 2001 (The growing problem of antibiotic resistance has health authorities extremely concerned. It is already the case that various germs are showing resistance to vancomycin (strong antibiotic), particularly to intestinal bacteria (Enterococcal species) among hospitalized patients.)

Finally, in 1988, the International Journal of Food Microbiology found oil of oregano to be an excellent antifungal, completely inhibiting the growth of the nine fungi tested. Other studies have been published that demonstrate the ability of oregano essential oil to kill yeast, including *Candida albicans*.

Oregano essential oil is a member of the Labiatae family. Native to Mediterranean regions, Oregano essential oil contains the following components:
- carvacrol (share 40-93%)
- gamma-terpinene (8-10%)
- p-cymene (5-10%)
- alpha-pinene
- myrcene
- thymol
- flavonoids
- caffeic acid derivatives The Physicians' Desk Reference for Herbal Medicines, Second Edition, also points out that there are various chemotypes with differing essential oil composition of thymol, linalool+terpinene-4-ol, linalool, caryophyllene+germacren D, or germacren D as chief components.

Oregano is also rich in minerals including calcium, magnesium, zinc, iron, potassium, copper, boron, and manganese and vitamins C, A (beta carotene), and niacin.

A drawback to oregano essential oil is that it is very potent, making it difficult for the average patient to control intake. As little as 3 drops can cause gastric upset. Moreover, while sake at appropriate dosages, Oregano essential oil, excessive dosages, is toxic to liver, kidneys and the nervous system.

Accordingly, consumer complaints regarding oregano essential oil is that it can cause, at a minimum, gastric upset and, worse, organ toxicity due to the difficult nature of dosage control. From a scientific standpoint there is interest in making as much of the oregano essential oil bioavailable as possible so as to get the maximum effect in a short amount of time without causing long-term deleterious side effects.

Attempts to address these issues have, until now, mainly revolved around purifying the oil to make it higher quality and then diluting it with either another oil or even following up ingestion with water. From a scientific standpoint, not much research has gone into increasing the bioavailability, thereby decreasing the required amount of oil required; thus, minimizing the potential negative effects of the oil while at the same time maximizing its benefits.

Accordingly, there is need for a composition that increases the bioavailability of oregano essential oil while at the same time shortening the time for absorption, and potentially reducing the amount of oil necessary to be consumed in order to obtain a desired result. Such a composition is provided for in the present invention.

IV. OBJECTS AND ADVANTAGES OF THE PRESENT INVENTION

It is an object of the present invention to provide a composition that enhances the bioavailability of oregano essential oil.

It is further an object of the present invention to provide a composition that shortens the time of absorption of oregano essential oil.

It is further an object of the present invention to provide a finely dispersed oregano essential oil.

It is further an object of the present invention to enable the reduction in the amount of a consumed oil oregano essential oil to be consumed.

The advantages offered by the present invention include but are not limited to maximizing the amount of bioavailable-consumed oil.

V. SUMMARY OF THE INVENTION

The present invention comprises a composition for increasing the bioavailability of oregano essential oil in humans and animals comprising adding a first emulsifier and a second emulsifier in a ratio ranging from about 1:1 to about 4:1, preferably, the first emulsifier and the second emulsifier are mixed in a ratio of about 2:1, and a consumable oil, such as flaxseed oil wherein with the final mixture of the three ingredients being in a ratio ranging from about 99:1 to about 9:1. Preferably, the ratio of the two emulsifiers together and the consumable oil is about 12.333:1. To the described mixture, add a further mixture oregano essential oil and the first emulsifier in a ration of about 1:1.

Preferably, the first emulsifier is polyoxyethylene sorbitan monooleate and the second emulsifier is tocopheryl polyethylene glycol succinate. The consumable oil can be of any type, with currently known sources being animal oils, vegetable oils, marine-based oils, and algae oils. The oils can be used either singly or in combination with one another. However, the Inventors have found that to limit allergic reaction, thereby taking advantage of oregano essential oil's purported anti-allergy affects, that a plant based oil, such as flaxseed oil be used.

Through the use of the inventive composition, a corollary to increasing the bioavailability of the consumable oil is that it reaches the blood steam more quickly than either purified oil alone or a prescription fish oil based medication.

In studies to measure the impact of the Invention, the inventive composition results in levels of oil blood stream concentrations, as measured by EPA levels (of a fish based oil), of about 250% over that of purified fish oil and about 400% over that of a prescription fish oil based medication, or about 0.253 mg/dl/hr versus 0.10 mg/dl/hr of purified fish oil and 0.06 mg/dl/hr for the prescription fish oil based medication based upon a gram intake.

There has been outlined, rather broadly, the more important features of the invention in order that the detailed description thereof that follows may be better understood, and in order that the present contribution to the art may be better appreciated. There are, of course, additional features of the invention that will be described hereinafter and that will form the subject matter of the invention.

VI. BRIEF DESCRIPTION OF THE DRAWINGS

VII. DETAILED DESCRIPTION OF THE PREFERRED EMBODIMENT

Figure 1:
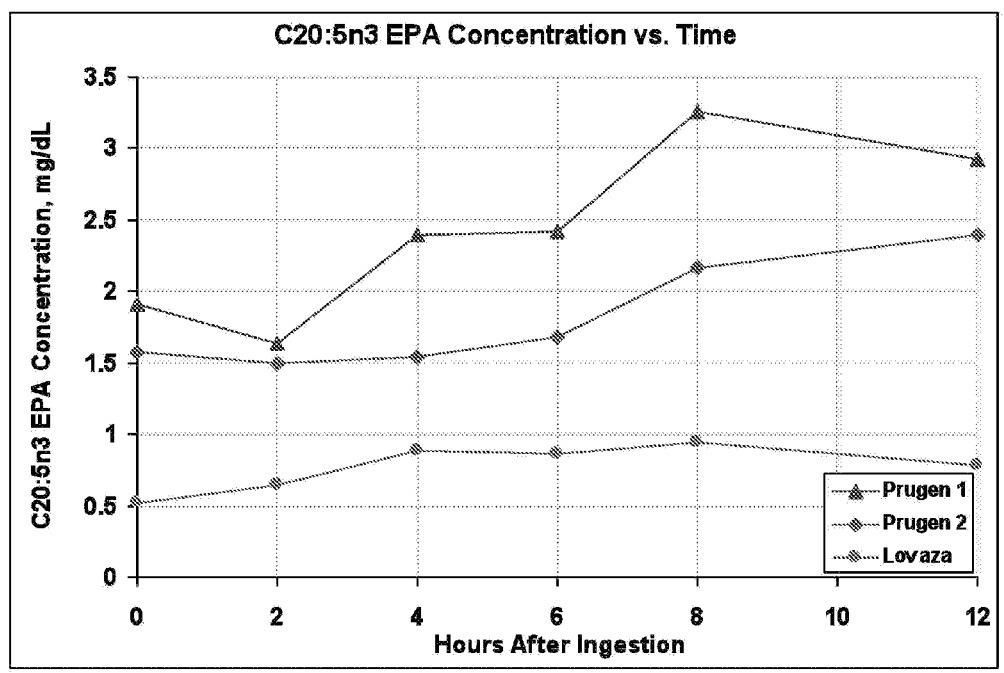
FIG. 1 depicts EPA blood level Concentration vs Time (Hrs) for the inventive composition compared with purified fish oil alone and with a prescription fish oil based medication.

Before explaining the preferred embodiment of the present invention in detail, it is to be understood that the present invention is not limited in its application to the details of formulations and arrangements of the components set forth in the following description. The present invention is capable of other embodiments and of being practiced and carried out in various ways. Also, it is to be understood that the phraseology and terminology employed herein are for the purpose of description and should not be regarded as limiting. It is also to be understood that where ranges are provided for the various agents and drug examples, they are approximate ranges and are not to be limiting except where noted otherwise.

The present invention addresses the problem of consumable oil bioavailability. To overcome limitations in absorption and bioavailability of such oils, the Inventors have discovered that creating a finely dispersed micro-emulsion in turn creates an increase in oil surface area per volume, thereby enabling greater gastrointestinal uptake of the oil. Through the use of emulsifiers that do not create a permanent binding to the oil, the bioavailability of the fish oil is increased.

The oregano essential oil used in the invention can be of any variety or quality. However, the Inventors have focused on high quality oregano essential oil that can be used in medical grade products. The combining oil, or "consumable oils," contemplated by the invention include oils from the vast variety of sources, including without limitation, marine (such as fish and crustacean), animal, plant, and algae. Principally, the oils have been selected for their Omega fatty acid content, and as is the current trend, Omega-3 fatty acids, although this is not a requirement for the effectiveness of the invention.

Among the Omega-3 fatty acids in current demand are eicosapentaenoic acid ("EPA") and docosahexaenoic acid ("DHA"). While Omega-3 fatty acids and EPA and DHA are used throughout, this is in no way meant to limit the scope and spirit of the invention. As those skilled in the arts will quickly understand, the principles taught herein will apply to any consumable oil, whether it contains Omega-3 fatty acid or not. For non-limiting example, other essential fatty acids include Omega-6 fatty acids, will also work well within the principles of the Invention. However, and as noted above, the Inventors have found that to limit allergic reaction, thereby taking advantage of oregano essential oil's purported anti-allergy affects, that a plant based oil, such as flaxseed oil be used.

To create a micro-emulsion adequate to provide the necessary results, the Inventors discovered that two emulsifiers are required. A first emulsifier should be a nonionic surfactant and emulsifier. There is a wide range of such emulsifiers from which to choose. Key to the selection is that the first emulsifier be suitable for human or animal ingestion (throughout, the terms consumption and ingestion are used interchangeable and mean to take orally.) The Inventors have discovered that the preferred first emulsifier is polyoxyethylene sorbitan monooleate.

A second emulsifier is also required. The Inventors have discovered that employing esterfied Vitamin E works well. While esterfied Vitamin E in its various forms may be employed in the invention, the Inventors have discovered that the preferred form is tocopheryl polyethylene glycol succinate.

Both of the preferred emulsifiers are well known in the industry. Polyoxyethylene sorbitan monooleate has been used for many years in the food and pharmaceutical industries. It is most commonly sold under the trade name polysorbate 80 and is widely available. It is approved by the U.S. Food and Drug Administration as an inactive ingredient and is well tolerated in oral compositions. Tocopheryl polyethylene glycol succinate is sold by several companies but was first developed by the Eastman Company and sold under the trademark 'Vitamin E TPGS NF.' It was developed as a water-soluble emulsifier to aid in the absorption of lipid-based drugs, such as cyclosporin. Since its invention, it has been used in many products.

However, until the present invention the combination use of polyoxyethylene sorbitan monooleate and tocopheryl polyethylene glycol succinate to enhance the bioavailability of consumable oils has not been taught.

Individually, each of these emulsifiers will cause at least some dispersion but it is the heretofore unknown mixture of the two emulsifiers and oil that creates the micro-emulsion necessary to increase the bioavailability of the oil. Using the Inventive Composition, a fine micro-emulsion is created that enables almost complete dispersion in water, a result unseen with either of the two emulsion separately or known in the prior art. The result is gained by the emulsion properties of the tocopheryl polyethylene glycol succinate to create a fine dispersion and the polyoxyethylene sorbitan monooleate to reduce further the interfacial tension that then enables an oil-in-water micro-emulsion of a level not heretofore seen in the art.

When considering the selection of emulsifiers to use in combination to create a suitable micro-emulsion, the Inventors discovered that surface activity of the emulsifiers on the oil was an important element. Increasing the surface area of the oil enabled increased bioavailability but only to a point. Once surface area exceeds a certain value, no additional benefit is gained in absorption and, therefore, bioavailability. In fact, bioavailability can be decreased.

To determine the suitable range of surface area activity, the Inventors employed hydrophilic lipophilic balance (HLB) values. HLB is a widely accepted method for providing a measure of the surface activity of organic molecules. HLB values for emulsifiers range from about 2 to about 40. The Inventors discovered that emulsifiers in the range of about 10 to about 30 are suitable for use with the invention, with a range of about 12 to about 16 providing the best results.

Polyoxyethylene sorbitan monooleate has an HLB value of about 15 and tocopheryl polyethylene glycol succinate has an HLB value about 13. Thus, the average HLB value for the combination of the two emulsifiers is about 14 when they are found in a 1:1 polyethylene glycol succinate:tocopheryl polyethylene glycol succinate ratio and about 14.6 when they are in a 4:1 polyethylene glycol succinate:tocopheryl polyethylene glycol succinate ratio. Accordingly, the preferred HLB range is from about 14 to about 14.6.

To demonstrate the effectiveness of the combination of these two emulsifiers and combined oils, the Inventors developed an experiment to illustrate the increased bioavailability of oils, using EPA and DHA as markers. In the experiment, subjects were cleared of blood stream detectable levels of EPA and DHA. The Human subjects were then randomly given either the Inventive composition, a purified fish oil, or a fish oil-based prescription medication under physician supervision. Blood level readings for both EPA and DHA were then taken at 2, 4, 6, 8, 10, and 12 hours.

Turning to FIG. 1, it can be seen that EPA levels for the inventive composition were significantly above those for both the purified fish oil and the prescription medication at every reading. The following table 1 illustrates the rate of blood level concentration (mg/dl/hr) for each of the three test materials:

TABLE 1

| Inventive Composition | Purified Fish oil | Prescription Medication |
|---|---|---|
| 0.253 | 0.10 | 0.06 |

Figure 2:
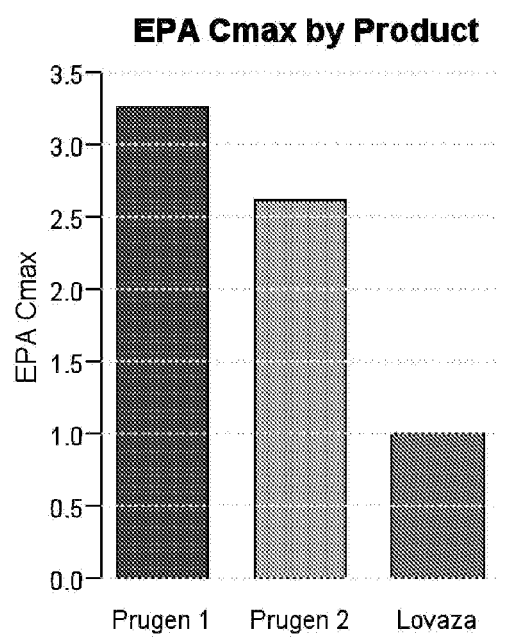
FIG. 2 depicts the maximum EPA blood level concentration for the inventive composition compared with purified fish oil alone and with a prescription fish oil based medication.

Turning to FIG. 2, it can be seen that the maximum blood concentration (Cmax) for the Inventive Composition EPA is also greater than that of the purified fish oil and the prescription medication. The following table 2 shows the Cmax (mg/dl) for each of the three test materials:

TABLE 2

| Inventive Composition | Purified Fish oil | Prescription Medication |
|---|---|---|
| 3.27 | 2.62 | 1.00 |

Figure 3:
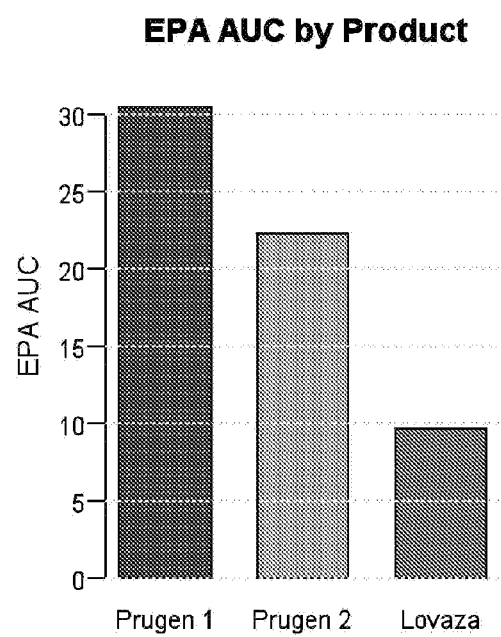
FIG. 3 depicts the maximum EPA AUC for the inventive composition compared with purified fish oil alone and with a prescription fish oil based medication

FIG. 3 illustrates the Area Under Curve (AUC) for the three test materials and, again demonstrates the superiority of the Inventive Composition. Table 3 shows the average AUC0-12 (mg/dl/hr) for the three test materials:

TABLE 3

| Inventive Composition | Purified Fish oil | Prescription Medication |
|---|---|---|
| 30.40 | 22.30 | 9.70 |

Figure 4:
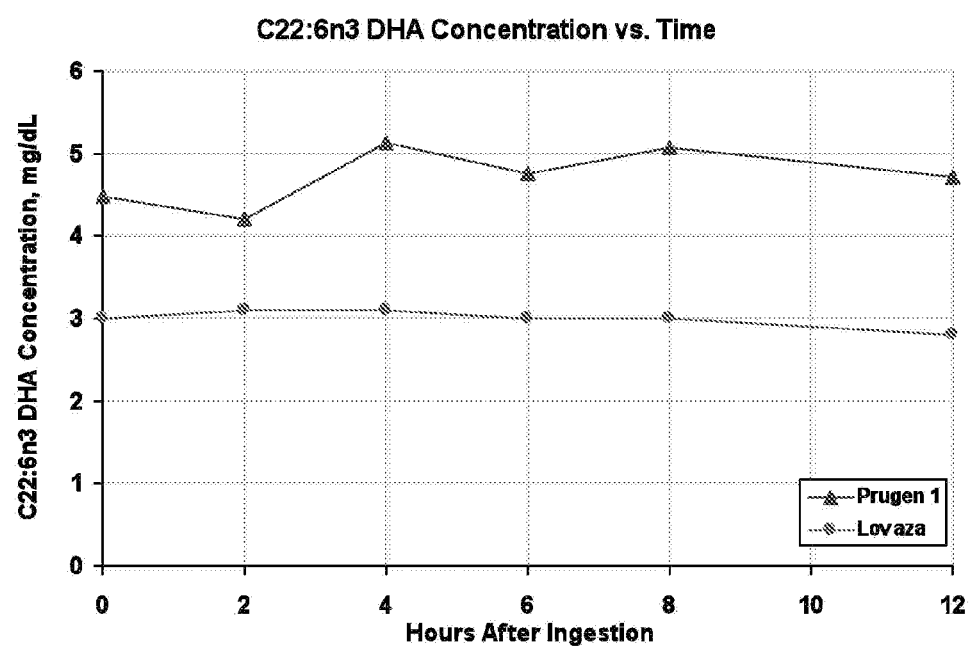
FIG. 4 depicts DHA blood level Concentration vs Time (hrs) for the inventive composition compared with prescription fish oil based medication.

DHA readings were then taken to further demonstrate the Inventive Composition effectiveness. Turning to FIG. 4, it can be seen that DHA levels for the inventive composition were significantly above those of the prescription medication at every reading.

Figure 5:
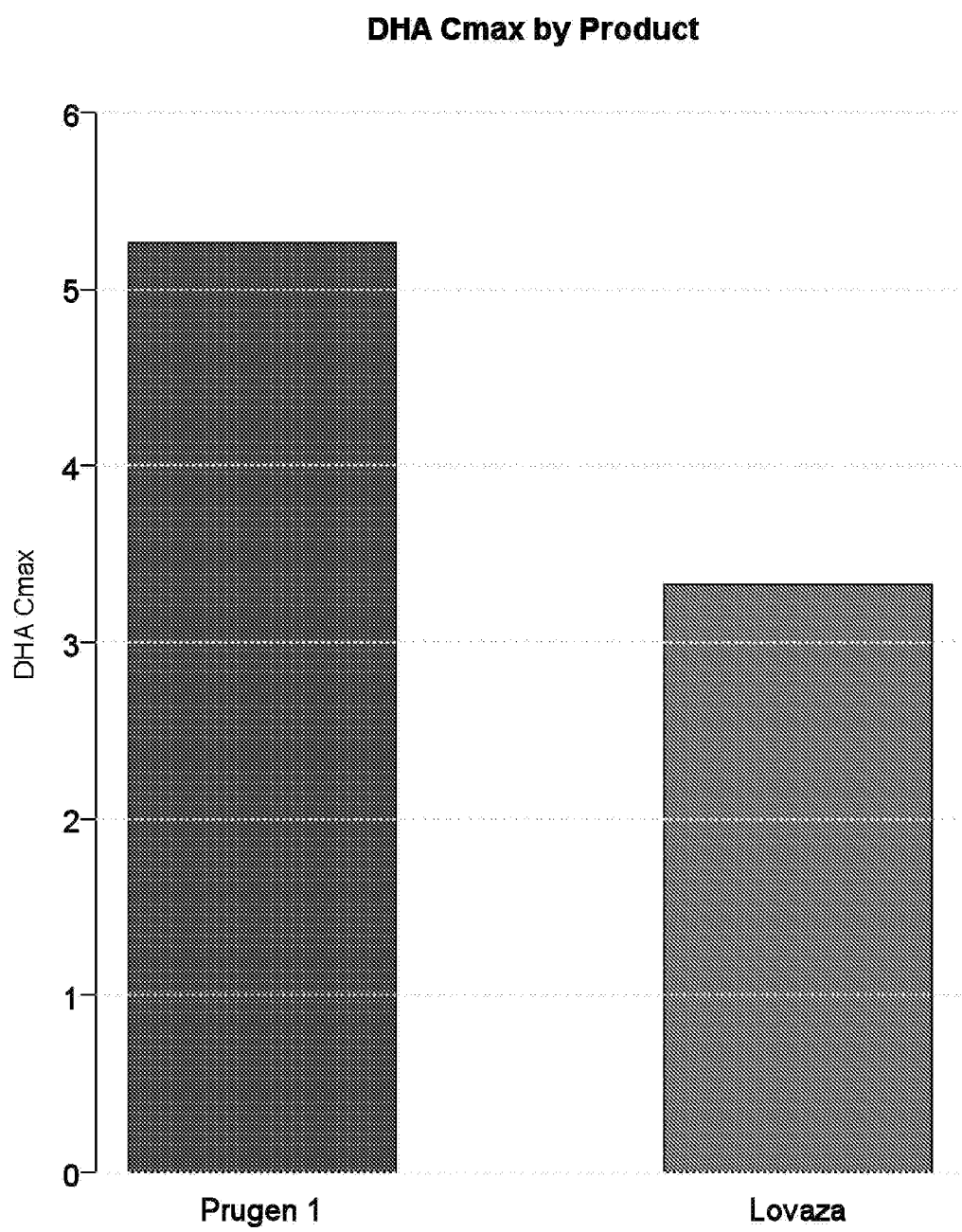
FIG. 5 depicts the maximum DHA blood level concentration for the inventive composition compared with prescription fish oil based medication.

Turning to FIG. 5, it can be seen that the maximum blood concentration (Cmax) for the Inventive Composition DHA is also greater than that of the prescription medication. The following table 4 shows the Cmax (mg/dl) for the two test materials:

TABLE 4

| Inventive Composition | Prescription Medication |
|---|---|
| 5.26 | 3.34 |

Figure 6:
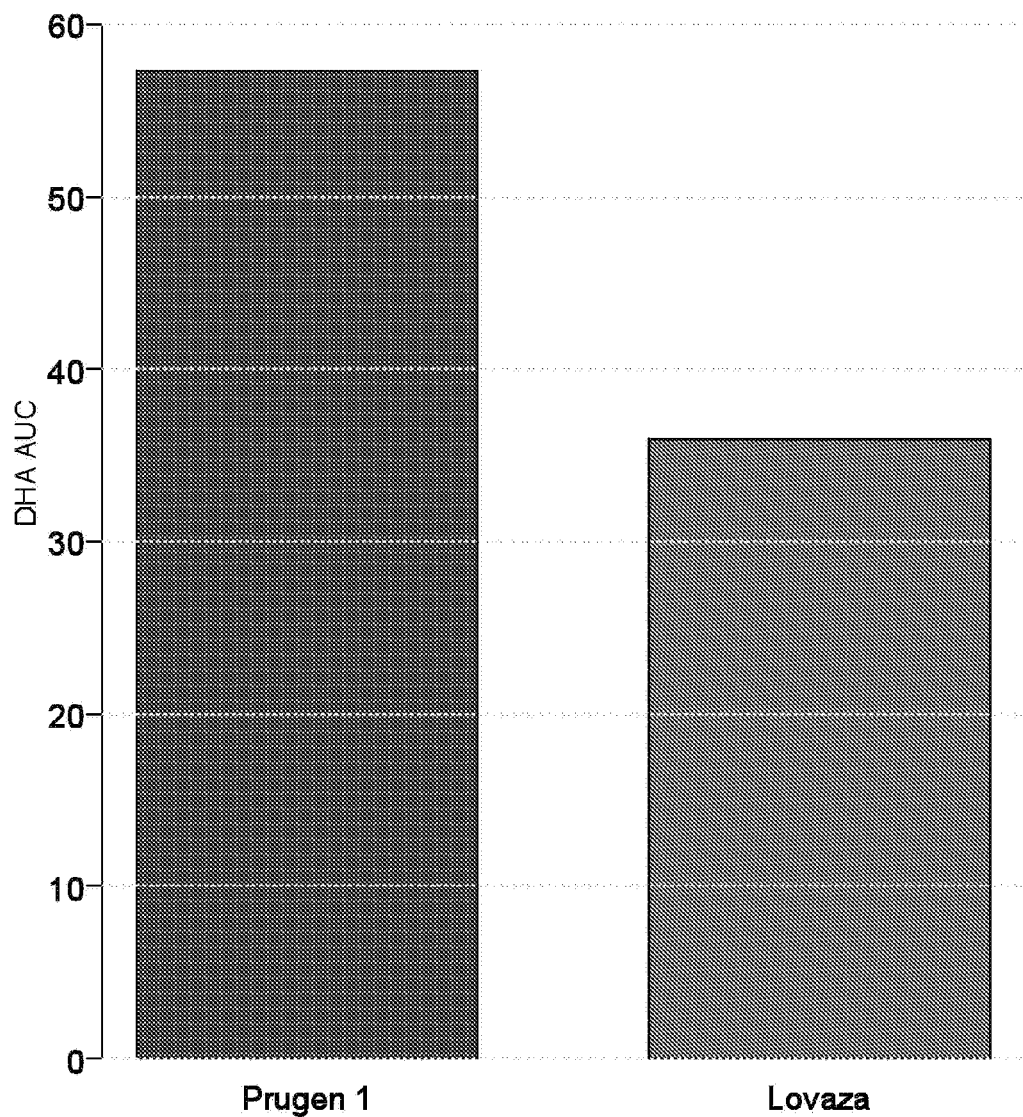
FIG. 6 depicts the maximum DHA AUC for the inventive composition compared with a prescription fish oil based medication.

FIG. 6 illustrates the Area Under Curve (AUC) for the two test materials and, again demonstrates the superiority of the Inventive Composition. The AUC0-12 for the Inventive Composition is 57.3 mg/di/hr. and for the prescription medication is 33.0 mg/di/hr.

In mixing of the two emulsifiers with oil to create a base solution to which oregano essential oil mixture can be added, the ratios of the two emulsifiers and oil in creating an end product with maximum effectiveness at a minimum use of emulsifiers have been considered. The Inventors have discovered that an emulsifier ratio in the range of polyoxyethylene sorbitan monooleate:tocopheryl polyethylene glycol succinate of about 1:1 to about 4:1 is useful. The preferred ratio is 2:1.

In mixing the three components together (consumable oil, first emulsifier, and second emulsifier) the emulsifier combination, which can be done as a separate step and added to the oil or individually added to the oil, the Inventors have discovered that the final mixture of oil:emulsifiers should be about 99:1 to about 9:1. Levels above 99:1 do not allow adequate dispersion to take place and level below 9:1 cause gelling of the oil-emulsifier combination. The preferred ratio is about 12.333:1.

The inventors have discovered due to its unique properties, oregano essential oil cannot be added directly into the base mixture—it will not disperse—even by adjusting the ratios of the various components. The reason for this is that low molecular weight compounds, terpenes such as oregano essential oil, and their derivatives require a terpenoid type molecule first for dispersion (such as a flaxseed oil/second emulsifier solution). Otherwise, if put into solution simultaneously with the first emulsifier and the second emulsifier, before it is saturated or solubolized, it will bind to the second emulsifier and not disperse.

Accordingly, to create a finely dispersed oregano essential oil product as described herein, it is necessary to create a base by adding a first emulsifier and a second emulsifier in a ratio ranging from about 1:1 to about 4:1, preferably, the first emulsifier and the second emulsifier are mixed in a ratio of about 2:1, and a consumable oil, such as flaxseed oil, wherein with the final mixture of the three ingredients being in a ratio ranging from about 99:1 to about 9:1. Preferably, the ratio of the two emulsifiers together and the consumable oil is about 12.333:1. To the described mixture, add a further mixture oregano essential oil and the first emulsifier in a ratio of about 1:1.

In the preferred embodiment, by following the described mixing procedures, the oregano essential oil will be diluted approximately 80%, thereby making consistently safe for consumption, which in turn, enables the opportunity for decreased side effects and increased benefits from the oregano essential oil properties.

It is to be understood, however, that even though numerous characteristics and advantages of the preferred and alternative embodiments have been set forth in the foregoing description, together with details of the structure and function of the embodiments, the disclosure is illustrative only, and changes may be made in detail within the principles of the invention to the full extent indicated by the broad general meaning of the terms in which the appended claims are expressed.

We claim:

1. A composition for increasing the bioavailability of oregano essential oil in humans and animals, formed by the process consisting of:

mixing a first emulsifier, a second emulsifier, and flax seed oil, to form a first mixture;

mixing oregano essential oil with the first emulsifier to form a second mixture; and combining the first mixture and the second mixture.

2. The composition of claim 1 wherein the first emulsifier and the second emulsifier are mixed in a ratio of about 2:1.

3. The composition of claim 1 wherein the first emulsifier is polyoxyethylene sorbitan monooleate.

4. The composition of claim 1 wherein the second emulsifier is tocopheryl polyethylene glycol succinate.

5. The composition of claim 1 wherein the first emulsifier and the second emulsifier have individual HLB values in the range of about 10 to about 30.

6. The composition of claim 5 wherein the first emulsifier and the second emulsifier have individual HLB values in the range of about 12 to about 16.

7. The composition of claim 5 wherein the first emulsifier and second emulsifier, when in combination, have a composite HLB value in the range of about 14 to about 14.6.

8. A composition for increasing the bioavailability of oregano essential oil in humans and animals, formed by the method consisting of mixing polyoxyethylene sorbitan monooleate, a second emulsifier, and flax seed oil, and adding to that a mixture oregano essential oil and polyoxyethylene sorbitan monooleate.

9. The composition of claim 8 wherein the polyoxyethylene sorbitan monooleate and the second emulsifier are mixed in a ratio of about 2:1.

10. The composition of claim 8 wherein the second emulsifier is tocopheryl polyethylene glycol succinate.

11. The composition of claim 8 wherein the polyoxyethylene sorbitan monooleate and the second emulsifier have individual HLB values in the range of about 10 to about 30.

12. The composition of claim 8 wherein the polyoxyethylene sorbitan monooleate and the second emulsifier have individual HLB values in the range of about 12 to about 16.

13. The composition of claim 8 wherein the polyoxyethylene sorbitan monooleate and second emulsifier, when in combination, have a composite HLB value in the range of about 14 to about 14.6.

* * * * *